United States Patent [19]

Schlüter et al.

[11] Patent Number: 4,467,816
[45] Date of Patent: Aug. 28, 1984

[54] DEVICE FOR COLLECTING CELL MATERIAL

[75] Inventors: Gert Schlüter, Liederbach; Jürgen Stahl, Frankfurt am Main, both of Fed. Rep. of Germany

[73] Assignee: Battelle-Institut e.V., Frankfurt am Main, Fed. Rep. of Germany

[21] Appl. No.: 285,843

[22] Filed: Jul. 22, 1981

Related U.S. Application Data

[63] Continuation of Ser. No. 22,865, Mar. 21, 1979, abandoned.

[30] Foreign Application Priority Data

Mar. 23, 1978 [DE] Fed. Rep. of Germany ....... 2812709

[51] Int. Cl.³ .............................................. A61B 1/00
[52] U.S. Cl. .................................... 128/756; 128/344
[58] Field of Search ............................. 128/756–758, 128/749–750, 344

[56] References Cited

U.S. PATENT DOCUMENTS

| | | | |
|---|---|---|---|
| 3,037,495 | 6/1962 | Naz | 128/2 |
| 3,095,871 | 7/1963 | Mann et al. | 128/2 |
| 3,168,092 | 2/1965 | Silverman | 128/1.2 |
| 3,433,214 | 3/1969 | Silverman | 128/2 |
| 3,525,329 | 8/1970 | Zeimer | 128/2 |
| 3,664,328 | 5/1972 | Moyle et al. | 128/2 B |
| 3,834,394 | 9/1974 | Hunter et al. | 128/325 |
| 3,850,176 | 11/1974 | Gottschalk | 128/325 |
| 3,881,464 | 5/1975 | Levene | 128/2 B |

FOREIGN PATENT DOCUMENTS 215350 10/1909 Fed. Rep. of Germany .

Primary Examiner—Kyle L. Howell
Assistant Examiner—Francis J. Jaworski
Attorney, Agent, or Firm—Fisher, Christen & Sabol

[57] ABSTRACT

A device for collecting cell material from a body cavity includes a guide tube and a cell sampler which is retractable into the guide tube, which has a front portion and a back portion. The cell sampler has the shape of an inflatable balloon which is retractable into itself and pulled over the end of the front portion of the guide tube. The device also has an inflation means for introducing gas into the sampler to inflate it. Retraction means, which passes through the guide tube and is connected with the inner wall of the balloon-type cell sampler, has been provided for retracting the cell sampler into the guide tube.

6 Claims, 4 Drawing Figures

DEVICE FOR COLLECTING CELL MATERIAL

This is a continuation of application Ser. No. 22,865, filed Mar. 21, 1979 and now abandoned.

BACKGROUND OF THIS INVENTION

1. Field of This Invention

Ths invention relates to a device for collecting cell material from body cavities, which composes a guide tube and a cell sampler which is retractable into the guide tube. In particular, this invention relates to an instrument for collecting cell material from the endometrium.

2. Prior Art

Examination of the endometrium is important for the diagnosis of premalignant and malignant tissue changes. It is also advisable, however, for case control after taking therapeutic measures, and for the functional diagnosis of the endometrium, which includes the assessment of hormonally induced effects or change due to pregnancy.

The examination of single cells is highly significant for clinical diagnosis, in particular for the early recognition of cancers. It is based on the principle of exfoliative cytology, i.e., on the examination of tumor cells which are spontaneously exfoliated from the cancer tissue or can be easily made to exfoliate. These cells must be easy to judge and clearly distinguishable from normal cells.

The problems of cell diagnosis on the endometrium are due to the fact, for example, that hormonally controlled proliferating processes may induce cell changes in the endometrium which make the detection of possibly existing atypical cells difficult. An additional problem is due to the difficulties in collecting endometrial cells, which in principle can be avoided only by an improved sampling technique.

In general, the endometrium is collected by means utilizing abrasion. For the evaluation of mucosal relief radiographs, on the other hand, collection of a tissue strip is sufficient. These methods involve surgery. However, numerous other methods for the collection of cells have been developed which need not be carried out under anesthesia. It should be noted, however, that all these collection methods and instruments require great skill and involve drawbacks which are essentially due to their mode of operation.

In the case of the conventional aspiration and irrigation methods (e.g., the Pistolet method or the Gravlee Jet-Wash method), the method of the material removed by aspiration or irrigation depends on the degree of exfoliation of the endometrium. Only such cells can be collected which lie on the surface of the endometrium in loose formations. The effect of the rinsing pressure on the tissue in the uterine lumen is non-uniform and uncontrollable. In addition, the cells cannot be collected from all regions, and the cells collected usually are in a poor state of conservation.

Swabbing with brush-type instruments (e.g., the Medhosa cannula and the device described in U.S. Pat. No. 3,881,464) does not involve significant advantages either, as the effect of such devices on the uterine mucosa cannot be controlled and the cell yield and the prevention of injuries depend on the skill of the operator. In addition, removal of the cells is difficult, as pieces of the mucosa remain trapped in the bristles of the devices.

Other swab cannulas (e.g., the Milan-Markey spiral) have a very harsh effect on the endometrium so that lesions or hemorrhages may result. Such instruments also do not permit controlled application and do not guarantee representative cell collection.

BROAD DESCRIPTION OF THIS INVENTION

An object of this invention is to provide a device for collecting cell material from a body cavity which overcomes the above-stated disadvantages of the prior art. Another object of this invention is to provide such a device which is easy to handle and yields sufficiently preserved and thus representative cell material, without involving the danger of injury to the tissue. A further object of this invention is a device which permits collection of cell material in the region from the endometrium to the tube zone. Other objects and advantages of this invention are set out herein or are obvious herefrom to one ordinarily skilled in the art.

The advantages and objects of this invention are achieved by the device of this invention.

This invention involves a device for collecting cell material from a body cavity comprised of a guide tube and a cell sampler, which is retractable into the guide tube. The cell sampler has the shape of a balloon that can be inflated and retracted into itself. The cell sampler (balloon shaped) is connected with (to) the opening of the guide tube. Traction (retraction) means, which passes through the guide tube and is connected to the inner wall of the balloon-type cell sampler, is provided for retracting the balloon-type cell sampler into the guide tube. The device of this invention works according to the principle of an imprint or "rub-off" method.

According to a preferred embodiment of this invention, the guide tube has a stepped shape (see FIG. 2) at its front end in order to enable easy and painless introduction.

The cells are collected on the surface of the balloon-type cell sampler which consists, for example, of natural rubber or a thermoplastic elastomer. The cell yield can be substantially increased if the surface of the balloon is roughened. The balloon is filled from the outside with a suitable gas or liquid, so that it can evaginate out of the guide tube to fit perfectly into the inner walls of the organ (body cavity).

The traction (retraction) means serves in particular to retract the evaginated balloon into itself and into the guide tube. Thus, the collected cell material is prevented from being stripped off when the device is taken out and foreign matter is prevented from being introduced.

In the simplest case, the traction means can be a thread of adequate length. According to a special embodiment of this invention, however, the traction means has the form of a drawbar which is connected to the upper pole on the inner wall of the balloon-type cell sampler. The connection can be effected by a thread fixed by one end to the upper part of the drawbar and by the other end to the inner wall of the cell sampler.

If the drawbar is hollow, the gas or the liquid can be introduced at the lower end of the drawbar. In such case the space between the guide tube and the drawbar is sealed at the upper part of the guide tube.

DETAILED DESCRIPTION OF THIS INVENTION

Other features, advantages and possibilities of application of this invention result from the following description of further details and from the drawings. The preferred embodiments are shown in the drawings and described below.

Figure 1:
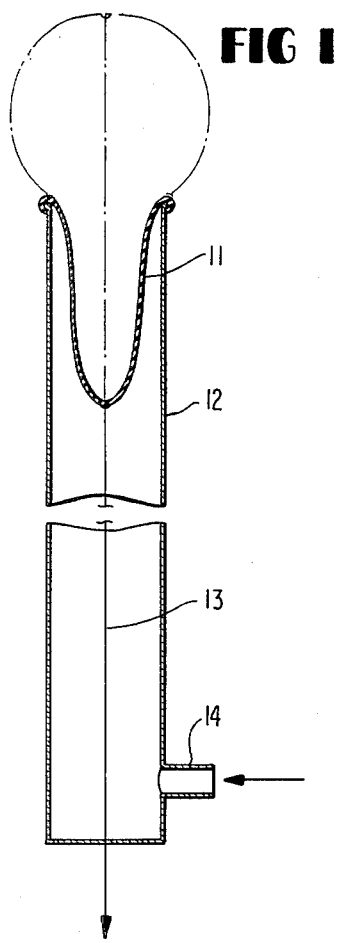
FIG. 1 is a schematic showing the principle of design of the device according to this invention.

FIG. 1 shows that cell sampler 11 is pulled over the front end of guide tube 12 such that a frictional connection is formed which is liquid- or air-tight. The connection can at the same time be so designed that balloon 11 can be removed after use. To retract balloon 11 into guide tube 12, traction means 13 has been provided. Retraction means 13 is centrally attached to the inner wall of balloon 11, preferably to its upper pole. After introduction of gas or a suitable liquid through nozzle 14, balloon-type cell sampler 11 can be evaginated after introduction into the organ (body cavity) so that it fits perfectly into the walls of the organ cavity to be examined. To prevent the gas or liquid from escaping, guide tube 12 is sealed at its lower end. The volume of the gas or the liquid which is introduced and thus the inflation of the balloon can be reduced or enlarged by an appropriate valve 23 at nozzle 14 or by an attached syringe, whereby the collection of cells from the walls of the organ is facilitated.

Figure 2:
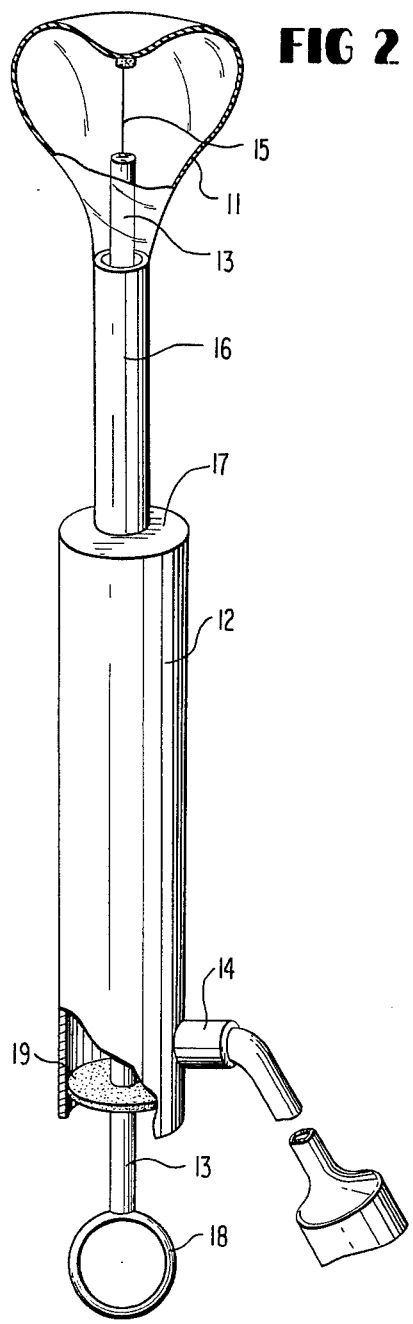
FIG. 2 is a partially cutaway elevational view where the drawbar is used as traction means and the gas or the liquid for inflating the cell sampler is introduced through the space between the guide tube and the drawbar.

FIG. 2 shows an advantageous embodiment. Drawbar 13 is movably mounted in guide tube 12. The upper end of drawbar 13 is connected with cell sampler 11 by means of thread 15. Direct connection of drawbar 13 with cell sampler 11 is also possible. The use of a short thread, however, prevents the wall of the organ to be examined from being injured when drawbar 13 is in the evaginated state of the cell sampler.

Prior to introducing the device into the organ, balloon 11 is inside part 16 of guide tube 12. Part 16 is smaller in diameter than guide tube 12 forming a stepped shape. Stop 17 can limit the depth of introduction of the device into the body cavity; it can be adjusted to any desired position. After introduction of the device into the body cavity by pushing operating element 18, drawbar 13 and thus also cell sampler 11 are pushed out of guide tube 12. The liquid or the gas is introduced via nozzle 14 through the space between guide tube 12 and traction element 13. Seal 19 mounted in the lower part of guide tube 12 prevents the gas or the liquid from escaping. Inflated balloon 11 assumes the shape of the organ, i.e., fits perfectly into its inner walls. By turning the instrument, simultaneous variation of the volume of the balloon and pushing the drawbar to and from, it is possible to produce additional rubbing motions of the surface of the cell sampler on the mucosa, which leads to a substantial increase in the cell collection yield.

Figure 3A:
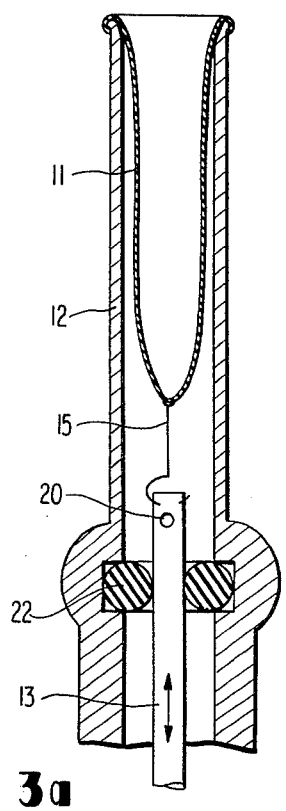
FIG. 3(a) is a longitudinal sectional view of the front end of the guide tube, with the drawbar being hollow.
Figure 3B:
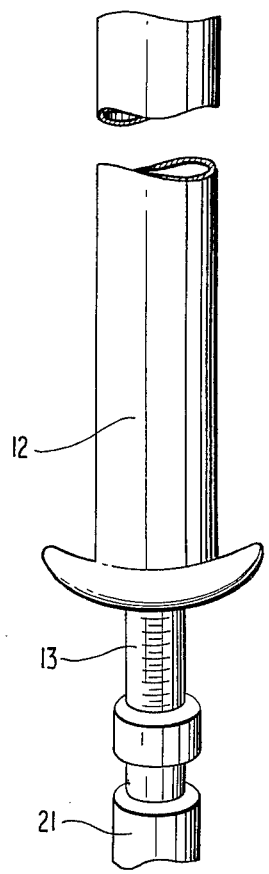
FIG. 3(b) is a longitudinal view of the design of the rear end of the guide tube, with the drawbar being hollow.

The drawbar can likewise be hollow—this design is shown in FIGS. 3(a) and 3(b). In this case, drawbar 13 is simultaneously also used to introduce the substance inflating the balloon. To this end, one or more outlet apertures 20 are provided in the upper part of drawbar 13—see FIG. 3(a). The rear end of drawbar 13 in suitably formed such that syringe 21 can be attached—see FIG. 3(b). To prevent the gas or liquid from escaping, gasket 22 has been provided, which is mounted in the space between guide tube 12 and drawbar 13.

The part of drawbar 13 which protrudes from guide tube 12 can be provided with marks permitting reading of the introduction (penetration) depth of the device.

The collected cell material can be removed from the walls of the balloon in different ways. When the balloon is reinflated, the cells can be directly transferred to the slide by means of a contact or imprint device, which permits the cell material to be assigned to the region from which it has been collected. It is also possible to rinse the entire surface of the balloon with a solution, e.g., an alcoholic fixing solution, and collect the whole cell material by centrifuging the solution.

The device according to this invention is particularly suited for collecting cells from body cavities which are accessible from the outside. The device according to this invention can also be used for initiating therapeutic measures, e.g., for hemostasis in hollow organs. Inflation of the balloon with a liquid, e.g., a physiological solution, leads to a substantial expansion of the balloon body, so that open blood vessels in the walls of the hollow organ can be compressed and the bleeding thereof stopped.

It is also possible to bring about the inflation of the balloon by an X-ray contrast medium, in order to check the position of the device by radiography or obtain important information about the inner structure of the organ.

By way of summary, this invention involves a device for collecting cell material from body cavities composed or consisting of a guide tube and a cell sampler which is retractable into the guide tube. The cell sampler has the shape of an inflatable balloon which is retractable into itself and pulled over the front end of the guide tube. Traction means, which passes through the guide tube and is connected with the inner wall of the balloon-type cell sampler, has been provided for retracting the cell sampler into the guide tube.

What is claimed is:

1. Device for collecting cell material from the endometrium which comprises:
   (a) a guide tube comprised of a first hollow portion and a second hollow portion, the second portion of the guide tube being narrower than the first portion of the guide tube and ending in a distal rim, the second portion of the guide tube being narrow enough to allow insertion thereof into the uterus, the first portion of the guide tube being too wide to allow insertion thereof into the uterus, the interface of the first portion and the second portion forming a ledge between the first portion and the second portion of the guide tube, the interface providing a stop and preventing insertion of the first portion of the guide tube into the uterus;
   (b) an elastic cell sampler having the shape of an inflatable balloon, which has a first section and a bulbous second section terminating in a distal end, the cell sampler being retractable into the second guide tube portion whereby the cell sampler is evaginated, the first section of the cell sampler being narrower than the bulbous second section when the cell sampler is in its normal, extended, non-evaginated position and in its inflated, extended, non-evaginated position, the bulbous second section of the cell sampler being wider than the guide tube, the end of the first section of the cell sampler being open, the open end of the first section of the cell sampler being pulled over the rim of the end of the second portion of the guide tube, and the outer sides of the cell sampler not contacting each other when it is in the retracted position or during the step of retracting it into itself from its inflated position or during the step of expanding it to its extended, non-evaginated position from its retracted position, and its retracted position being situated inside of the guide tube and its extended inflated position being situated external to the end of the second portion of the guide tube;

(c) means for introducing a gas or liquid to inflate the cell sampler and for allowing the gas or liquid to exit, to the extent required, from the cell sampler and guide tube as the inflated cell sampler is concurrently deflated and retracted into the guide tube, the inflation means being attached to the first hollow portion of the guide tube; and (d) manipulation means for the cell sampler, the manipulation means being located in the guide tube, having one end thereof extending into the cell sampler, when the cell sampler is in its extended, non-evaginated position, with such end thereof being attached to the inside surface of the end of the bulbous second section of the cell sampler, and having the other end thereof protruding out of the other end of the guide tube, the manipulation means providing means for retracting the cell sampler, when it is in its normal, extended, non-evaginated position, into the guide tube, the inflation means allowing deflation of the inflated cell sampler as the cell sampler is retracted, extension of the evaginated cell sampler into the normal, extended, non-evaginated position and inflation of the cell sampler when in the normal, extended, non-evaginated position to effect collection of cell material.

2. Device as claimed in claim 1 wherein the bulbous section of the cell sampler has a roughened surface.

3. Device as claimed in claim 1 wherein the guide tube is sealed in the end region of its second portion with a seal which allows slidable movement therethrough by the manipulation means.

4. Device as claimed in claim 1 wherein the means for introducing gas or liquid includes a nozzle attached to the second portion of the guide tube and a valve attached to the nozzle.

5. Device as claimed in claim 4 wherein the manipulation means is a drawbar.

6. Process for collecting cell material from the endometrium using a cell collecting device comprising;

(a) a guide tube comprised of a first hollow portion and a second hollow portion, the second portion of the guide tube being narrower than the first portion of the guide tube and ending in a distal rim, the second portion of the guide tube being narrow enough to allow insertion thereof into the uterus, the first portion of the guide tube being too wide to allow insertion thereof into the uterus, the interface of the first portion and the second portion forming a ledge between the first portion and the second portion of the guide tube, the interface providing a stop and preventing insertion of the first portion of the guide tube into the uterus;

(b) an elastic cell sampler having the shape of an inflatable balloon, which has a first section and a bulbous second section terminating in a distal end, the cell sampler being retractable into the second guide tube portion whereby the cell sampler is evaginated, the first section of the cell sampler being narrower than the bulbous second section when the cell sampler is in its normal, extended, non-evaginated position and in its inflated, extended, non-evaginated position, the bulbous second section of the cell sampler being wider than the guide tube, the end of the first section of the cell sampler being open, the open end of the first section of the cell sampler being pulled over the rim of the end of the second portion of the guide tube, and the outer sides of the cell sampler not contacting each other when it is in the retracted position or during the step of retracting it into itself from its inflated position or during the step of expanding it to its extended, non-evaginated position from its retracted position, and its retracted position being situated inside of the guide tube and its extended inflated position being situated external to the end of the second portion of the guide tube;

(c) means for introducing a gas or liquid to inflate the cell sampler and for allowing the gas or liquid to exit, to the extent required, from the cell sampler and guide tube as the inflated cell sampler is concurrently deflated and retracted into the guide tube, the inflation means being attached to the first hollow portion of the guide tube; and (d) manipulation means for the cell sampler, the manipulation means being located in the guide tube, having one end thereof extending into the cell sampler, when the cell sampler is in its extended, non-evaginated position, with such end thereof being attached to the inside surface of the end of the bulbous second section of the cell sampler, and having the other end thereof protruding out of the other end of the guide tube, the manipulation means providing means for retracting he cell sampler, when it is in its normal, extended, non-evaginated position, into the guide tube, the inflation means allowing deflation of the inflated cell sampler as the cell sampler is retracted, extension of the evaginated cell sampler into the normal, extended, non-evaginated position and inflation of the cell sampler when in the normal, extended, non-evaginated position to effect collection of cell material, said process comprising inserting the second portion of the guide tube of the said device into a vagina and on into a uterus, moving the inflatable cell sampler out of the guide tube into the uterus, inflating the inflatable cell sampler concurrently as it is moved out of the guide tube so that the bulbous section of the cell sampler contracts the endometrium of the uterus, whereby a sample of cell material from the endometrium attaches to the bulbous section of the inflatable cell sampler, concurrently deflating and retracting the inflatable cell sampler into the guide tube in such a manner that the sides of the inflatable cell sampler do not touch each other, and removing the guide tube from the uterus and vagina.

* * * * *